United States Patent [19]
Sovak et al.

[11] Patent Number: 4,954,348
[45] Date of Patent: Sep. 4, 1990

[54] NON-IONIC POLYOL CONTRAST MEDIA FROM IONIC CONTRAST MEDIA

[75] Inventors: Milos Sovak, Rancho Santa Fe, Calif.; Ramachandran Ranganathan, Princeton, N.J.

[73] Assignee: Cook Imaging Corporation, Bloomington, Ind.

[21] Appl. No.: 214,663

[22] Filed: Jul. 1, 1988

Related U.S. Application Data

[60] Division of Ser. No. 110,110, Oct. 13, 1987, abandoned, which is a continuation of Ser. No. 894,934, Aug. 8, 1986, abandoned, which is a continuation-in-part of Ser. No. 764,274, Aug. 9, 1985, abandoned.

[51] Int. Cl.$^5$ .................. C07C 237/46; A61K 31/165; A61K 49/04
[52] U.S. Cl. .......................................... 424/5; 564/153
[58] Field of Search .............................. 564/153; 424/5

[56] References Cited

U.S. PATENT DOCUMENTS

| 3,701,771 | 10/1972 | Almen et al. | 424/5 X |
| 3,867,431 | 2/1975 | Felder et al. | 424/5 X |
| 4,250,113 | 2/1981 | Nordal et al. | 424/5 X |
| 4,364,921 | 12/1982 | Speck et al. | 424/5 |
| 4,396,598 | 8/1983 | Lin | 424/5 |
| 4,547,357 | 10/1985 | Pfeiffer et al. | 424/5 |

OTHER PUBLICATIONS

Schneider et al., *Functional and Morphological Affects of Ioxitol, Iohexol and Diatrizoate on Endothelial Cells.*
Dawson et al., *British J. of Radiology*, 56, 653-656 (Sep. 1983).
Karcher et al., *Acute Intravenous Toxicity Study in Mice: Ioxitol* (7/1987).
Raicher et al., *Acute Intravenous Toxicity Study in Rats: Ioxitol* (7/1987).
Sovak, *Handbook of Exp. Pharmacology*, vol. 73, pp. 1–22 (1984).
Parvez et al., *Contrast Media = Biological Effects and Clinical Application*, vol. I, pp. 47–66.
Speck et al., *Investigative Radiology*, Nov. 1980, vol. 15, pp. S335–339.
Wilcox et al., *Neuroradiology*, (1986), 28: 271–274.
Thomsen et al., *DO Contrast Media Aggravat Fanconi Syndrome in Rats.*
Thomsen et al., *Effects of Intravenous Diatrizoate, Iohexol and Ioxitol on Renal Functions in the Rat.*
Siegle, *Investigative Radiology*, Oct. 1986, vol. 21 pp. 779–781.
Parvez et al., *Affect of a New Nonionic Contrast Agent, Ioxitol, on Erythrocyte Morphology.*
Sovak et al., *Current Contrast Media and Ioxitol: Comparative Evaluation of Vascular Pain by Aversion Conditioning.*

*Primary Examiner*—Carolyn S. Elmore
*Attorney, Agent, or Firm*—Woodward, Emhardt, Naughton, Moriarty & McNett

[57] ABSTRACT

Novel non-ionic contrast media of a hitherto unknown combination of low osmolality and low viscosity are efficiently prepared from generally available ionic contrast media or non-iodinated precursors. Particularly, polyhydroxyhalo-hydrocarbons are employed with a triiodo-substituted acylamido benzoic acids in aqueous weakly basic media to selectively substitute the amido nitrogen, followed by activation of the carboxyl group for amide formation.

2 Claims, No Drawings

NON-IONIC POLYOL CONTRAST MEDIA FROM IONIC CONTRAST MEDIA

This is Ser. No. 110,110 filed Oct. 13, 1987, which is a continuation of application Ser. No. 894,934, filed Aug. 8, 1986, which is a continuation-in-part of application Ser. No. 764,274, filed Aug. 9, 1985, all now abandoned.

BACKGROUND OF THE INVENTION

1. Field of the Invention

This invention is related to contrast media used in the field of medical imaging with X-rays. It is particularly related to non-ionic contrast media.

2. Description of the Background

Medical imaging with X-rays depends to a great extent upon radiographic contrast media (CM). An ideal CM, designed to mix with the body fluids, should be economically feasible, chemically stable, highly water soluble, readily injectable, and biologically inert. CM of the prior art, generally based on salts of derivatized triiodinated benzene moieties, meet the first four criteria, but they induce adverse clinical effects. Such toxicity extends from their ionicity, solution hyperosmolality vis-a-vis the body fluids and chemotoxicity, reflecting their relatively high hydrophobicity.

Non-ionic, less hyperosmolal, less hydrophobic but more costly compounds exist, of which Iohexol/Iopamidol/Metrizamide are used clinically in the United States. Metrizamide suffers from hydrolytic instability and thus must be dispensed in lyophilized form and reconstituted prior to use. Solutions of some other non-ionic, stable CM have, however, higher osmolality and can thus elicit pain when injected into the arteries. Other compounds are, at elevated concentrations, not persistently water soluble. All current non-ionic CM, while less toxic than the prior art, are much more costly.

Consequently, despite the large number of compounds which have been prepared, there is substantial interest in producing a non-ionic CM improved both pharmacologically and economically. To this end, it is essential once the ring has been iodinated that subsequent steps are few and have high yields. Furthermore, the iodinated substrate, as well as the reactants that are employed for additional functionalization, should be inexpensive.

Brief Description of the Relevant Literature

There is extensive patent literature concerned with non-ionic contrast media and their method of preparation. See particularly, U.S. Pat. Nos. 4,364,921: 4,341,756; 4,250,113: 4,021,.481 4,001,323, 3,702,866: 3,701,771: and 3,622,616. See also, "Radiocontrast Agents", Volume 73 of the Handbook of Experimental Pharmacology, Springer, New York, 1985, which provides a comprehensive review of the field as of the time of publication.

SUMMARY OF THE INVENTION

Non-ionic contrast media are prepared by selective and efficient polyhydroxyalkylation of the nitrogen of an acylamido substituted triiodobenzoic acid with a polyhydroxyalkyl halide in an aqueous medium under weakly basic conditions. The polyhydroxyalkylated acid is then activated for formation of functionalized benzamides. Alternatively, N-polyhydroxyalkylation can be carried out on fully functionalized benzamides made from ionic or non-ionic precursors. The methodologies provide a novel and efficient synthetic approach to novel non-ionic contrast media of low viscosity and low osmolality, a combination desirable for painless vascular injections, which has not previously been obtained in a clinically useful contrast medium.

DESCRIPTION OF THE SPECIFIC EMBODIMENTS

Novel methods are provided for producing non-ionic contrast media employing triiodo persubstituted acylamidobenzoic acids as starting materials, preferably available as an ionic contrast media. The method involves selective and efficient alkylation of the nitrogen of the acylamido group with a halohydrin under weakly basic conditions in an aqueous medium, followed by protection of hydroxyl groups, activation of the benzoic acid group and amidation of the activated benzoic acid group. The protective groups will then be removed to provide the final product. The synthetic strategy employs readily available reagents that are for the most part inexpensive and results in high yields of readily purifiable intermediates and final product.

The starting materials are 5-acylamido substituted triiodobenzoic acids, where the 3-position will be substituted with a substituted amino group or a carboxamido group The starting materials will normally have at least about 10 carbon atoms, and usually from 0 to 2, more usually from 0 to 1, hydroxyl group. The product will usually have less than 20 carbon atoms, more usually fewer than about 18 carbon atoms, and will have at least three nitrogen atoms, of which at least one will be substituted to an annular carbon atom while one or both of the nitrogen atoms may be amido Acyl groups bound to nitrogen will generally have from 1 to 4 carbon atoms, usually from 2 to 3 carbon atoms, and from 0 to 3 oxy substituents, more usually from 0 to 2 oxy substituents. Alkyl substituents will be generally of from 1 to 3 carbon atoms, more usually of from 1 to 2 carbon atoms, and having from 0 to 3 hydroxyl groups, more usually from 0 to 2 hydroxyl groups.

The following flow chart indicates one synthetic strategy. TIB intends triiodobenzene, and the vertical line indicates which groups associated with the horizontal lines are bound at the 1, 3, and 5 positions, respectively. The numbers over the arrows indicate the reaction, with the legend indicating the reagents and conditions for the reaction.

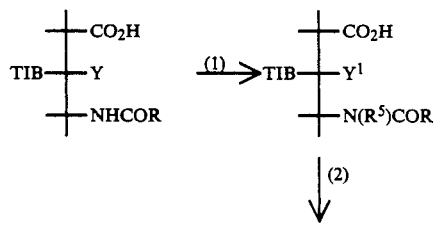

-continued

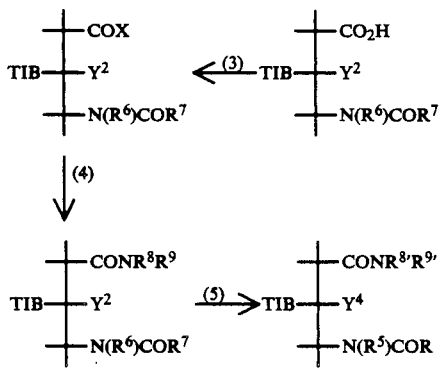

(1) halohydrin of 2 to 5 carbon atoms and 1 to 4 oxy groups; aqueous base, pH 9–13, 60–100° C., 0.5–6 hr.

(2) AcZ, Z = chloro or AcO, where Ac is an acyl group of from 2 to 3 carbon atoms; tert.-amine, 50–80° C., 1–6 hr.

(3) G—Cl (G-inorganic or organic acyl group); 50–80° C.; 0.25–3 hr.

(4) HNR$^8$R$^9$; tert.-amine, 35–75° C.

(5) (a) OH$^-$; (b) neutralization, optionally acidification when acetonides are present.

The symbols are defined as follows:
TIB=2,4,6-triiodobenzene:
Y=NR$^1$R$^2$ or CONR$^3$R$^4$ or CH$_2$NR$^2$COR$^3$
R=an aliphatic group of from 1 to 3, usually 2 to 3 carbon atoms, having from 0 to 2, usually 0 to 1 oxy groups:
R$^1$=hydrogen, an aliphatic group of from 1 to 3, usually 1 to 2 carbon atoms, having from 0 to 2 usually 0 to 1 oxy groups, an aliphatic acyl group of from 1 to 3, usually 1 to 2 carbon atoms, and from 0 to 2, usually 0 to 1 oxy groups:
R$^2$=the same or different from R$^1$, usually R$^2$ will be hydrogen or an aliphatic group: at least one of R$^1$ and R$^2$ being other than hydrogen;
R$^3$=hydrogen or an aliphatic group of from 1 to 3, usually 1 to 2 carbon atoms, having from 0 to 2, usually 0 to 1, oxy groups or acyloxy groups:
R$^4$=the same or different from R$^3$, usually hydrogen:
R$^5$=mono- or polyoxyalkyl from 2 to 5, usually 2 to 4, preferably 3 to 4 carbon toms, having from 1 to 4, usually 1 to 2 oxy groups:
Y$^1$=NR$^1$R$^{2'}$ or CONR$^3$R$^4$;
R$^{2'}$=the same as R$^2$ with the proviso that when R$^2$ is hydrogen and R$^1$ is acyl or an aliphatic group, then R$^{2'}$ includes mono- or polyoxyalkyl of from 2 to 5, usually 2 to 4, preferably 3 to 4 carbon atoms having from 1 to 3, usually 1 to 2 oxy groups:
R$^6$=the same as R$^5$, except all hydroxyl groups of R$^5$ are acyloxy groups, where Ac is bonded to the hydroxyl oxygen:
R$^7$=the same as R, except all hydroxyl groups of R$^5$ are acyloxy groups, where Ac is bonded to the hydroxyl oxygen:
Y$^2$=the same as Y$^1$, except all hydroxyl groups of Y$^1$ are acyloxy groups, where Ac is bonded to the hydroxyl oxygen;
R$^8$ and R$^9$ =the same or different and are hydrogen or alkyl of from 1 to 4 carbon atoms having 0 to 3, usually 1 to 3 oxy groups, the total number of carbon atoms being not greater than about 6, usually not greater than about 4;
R$^{8'}$ and R$^{9'}$=the same as R$^8$ and R$^9$ except they exclude alkoxy groups as substituents:
Ac=an aliphatic acyl group of 2 to 3 carbon atoms, particularly acetyl;
X=halo or 2-oxypyridyl, N-oxysuccinimidyl or isoureido:
Y$^4$=Y$^1$ or Y.

Each of the stages will now be considered in detail. The starting compound will be an acylamido triiodo substituted benzoic acid, where the other substituent is a carboxamido group or an acylamido group. Desirably, the starting materials may be ionic contrast media or their iodinated precursors, readily commercially available and inexpensive. Such compounds include derivatives of triiodo-3,5-diaminobenzoic acid, diatrizoate, 3,5-diacetamido-2,4,6-triiodobenzoic acid, and metrizoate, the N-mono-methyl derivative of diatrizoate, and derivatives of 5-aminoisophthalic acid, iothalamate, 5-acetamido-2,4,6-triiodo-N-methylisophthalamic acid and ioxithalamic acid, 5-acetamido-2,4,6-triiodo-N-(2-hydroxyethyl)-isophthalamic acid or its immediate precursor, the corresponding N-(2-acetoxyethyl) compound. While generally available ionic contrast media are preferred as starting materials, any of the triiodobenzoic acid derivatives substituted at the 3 and 5 positions with amino and carboxy groups having various useful substituents may be employed.

The method will now be described in further detail. The first step is the reaction of the acylamido substituted triiodobenzoic acid with a halohydrin of from 2 to 5 carbon atoms, usually 3 to 4 carbon atoms, particularly a chlorohydrin, preferably where the chloro group is a primary or secondary chloro group, there being from 1 to 4 oxy groups, at least one of the oxy groups being hydroxy to provide a vicinal halohydrin. The reaction will be carried out in aqueous base, normally a basic solution of at least pH 9, generally from about pH 9 to pH 14, more usually from about pH 9.5 to pH 13.5. Stoichiometric amounts of the halohydrin may be employed, usually a small excess, not exceeding two molar excess, usually not exceeding one molar excess. The pH is maintained during the course of the reaction. Temperatures will normally be at least about 45° C. and not exceeding about 100° C., preferably between 45° C. to 95° C. The reaction is carried out until completion, which can be monitored by TLC or HPLC. Generally, less than 2 hr is required, frequently less than 1 hr An aqueous medium is employed which may or may not have cosolvents. Since an aqueous medium suffices, cosolvents will usually not be employed.

At completion of the reaction, the product need not be isolated and purified, rather, the medium may be neutralized to a mildly acidic pH, usually from about pH 4 to pH 6 and the solvents removed, e.g., azeotroped with an appropriate cosolvent, e.g., pyridine or toluene. The residue may then be used directly in the next step.

The next stage is the protection stage, where hydroxyl groups will be reacted with an appropriate reagent which is stable under the reaction conditions of the next successive steps. Since the next successive steps will involve acidic reagents, the protective groups will be those which will be able to survive the subsequent reactions. The reagents employed for the protection will of course be reactive so as to react with the hydroxyl groups and any available amino group, will not interfere with the reactions of the carboxyl group to form an amide, and will allow for easy recovery of the product free of the protective groups. Furthermore, since economics are important to the synthetic strategy, normally inexpensive groups will be employed. However, other groups could be used less efficiently and less economically.

Of particular interest is the use of acylhalides and acyl anhydrides of from 1 to 3, preferably 2 carbon atoms, particularly acetic anhydride. With acetic anhydride, the anhydride may serve as the solvent and will therefore be in substantial excess, the particular amount will usually be at least about 2- to 3-fold molar excess. With other agents, the agents themselves may either be used as the solvent, when appropriate, or an inert solvent may be employed such as acetonitrile, ethyl acetate or dichloromethane. In addition to the anhydride, an activating catalyst will be employed, particularly a tertiary amino compound, more particularly pyridine. The temperatures will be higher than room temperature, generally in the range of about 40°–60° C., and the reaction will usually require about 1–6 hr, depending upon the particular reagent and the size of the reaction batch. The course of the reaction may be followed by thin-layer chromatography (TLC).

Workup will normally involve removal of the solvents by evaporation and azeotroping, as appropriate. The residue may then be dissolved in water and the aqueous layer extracted with a water immiscible polar organic solvent, e.g., an ester, conveniently ethyl acetate, in admixture with a nonpolar solvent, such as toluene. The aqueous layer may then be acidified to precipitate the hydroxy-protected benzoic acid and the precipitate dissolved into an organic extractant, conveniently the same organic extractant, and the organic extracts combined. The product can then be isolated in conventional ways.

The hydroxy-protected benzoic acid compound is then activated, so as to be reactive with an aliphatic amine. A variety of ways are available for activation of the carboxy groups. 0-Acylureas can be formed, by employing carbodiimides or the like. Active esters may be prepared, such as N-oxysuccinimide, 2-acyloxypyridyl, nitrophenyl, chlorophenyl, or the like. While the particular manner in which the carboxyl group is activated is not critical to this invention, the preferred method is to prepare the acyl chloride employing an inorganic or organic acid halide, particularly an inorganic halide such as thionyl chloride, sulfuryl chloride, phosphorus pentachloride, or the like. Of particular interest is the use of thionyl chloride, where the thionyl chloride may be used as the solvent and be present in excess, usually at least about 1 to 4 molar excess, and the reactant dissolved in the thionyl chloride. Alternatively, the compound may be dissolved in an inert solvent such as dichloromethane or ethyl acetate and thionyl chloride employed in a small excess, usually 2 to 4 molar excess. The mixture will be heated at an elevated temperature, generally from about 50°–75° C. for a sufficient time for the reaction to go to completion, generally from about 0.25 to 3 hr. The reaction may be monitored by TLC. The thionyl chloride and other incipient solvents may then be removed by evaporation and appropriate azeotroping of the residue to remove any residual thionyl chloride, and the resulting product dissolved in an inert polar organic solvent, e.g., an ester, followed by washing with bicarbonate and drying of the organic layer.

The activated carboxyl, particularly the acyl halide, may then be combined in an inert organic polar solvent, conveniently an ether or an amide, more conveniently dioxane or dimethylacetamide, with an acid-neutralizing compound, conveniently a tertiary amino compound, or in a mixture of an inert organic polar solvent, preferably acetone or dichloromethane (which gives two phases) with water, in the presence of an inorganic base, preferably a carbonate or bicarbonate such as $Na_2CO_3$, $K_2CO_3$, or $NaHCO_3$. The amino compound may be ammonia or alkylamino of from 1 to 4 carbon atoms, having from 0 to 3, usually from 0 to 2 hydroxy groups, which may be protected or unprotected, when protected, as ethers, particularly acetals or ketals, more particularly acetonide. The reaction is carried out under mild conditions at room temperature or at an elevated temperature, generally from about 40°–70° C. until completion, which will usually require about 0.5 hr and less than 12 hr, usually less than 9 hr.

The workup follows generally the same procedure as prior workups, in that the solvents are evaporated, the product dissolved in an appropriate polar organic solvent and washed with water with or without added sodium chloride. The organic layers may then be dried and the solvent removed by evaporation. In each instance, the isolation steps are conventional.

The hydroxyl groups are then deprotected employing a basic medium, usually basic alkanolic medium, particularly methanol, the pH being at least about 10 and hydroxyl concentration being less than 1 normal. The reaction may be carried out under mild conditions, usually ambient temperatures being satisfactory, the reaction usually being complete in less than about 2 hr. Volatile materials may then be removed by evaporation and the residue neutralized with aqueous acid, also under ambient conditions. Conveniently, a pH of 1 to 2 may be employed to remove acetonide functions when they are present. Desirably, the product may be further purified by desalting with an appropriate ion exchange resin.

A wide variety of compounds may be made in accordance with the subject invention. Of particular interest are the novel compounds 5-(2,3-dihydroxypropylacetamido)-2,4,6-triiodo-N-(2,3-dihydroxypropyl)-N'-(2-hydroxyethyl)-isophthalamide (compound VIII in the Experimental Section) and 5-(N-2,3-dihydroxypropylacetamido)-2,4,6,-triiodo-N-methyl-N'-(1,3,4-trihydroxy-threo-but-2-yl)-isophthalamide (compound XVIII in the Experimental Section).

These particular compounds are found to have excellent properties as to toxicity, water solubility, osmolality, stability, viscosity and the like, factors predominantly important in angio- and urography.

It is also possible to produce novel non-ionic polyol contrast media beginning with non-iodinated compounds. For example, a 5-amino-N-(mono or poly)hydroxyalkyl-N'-(mono or poly)hydroxyalkylisophthalamide can be reacted with an iodine source, such as $KICl_2$ in an aqueous acid solution with heating. In this and the other compounds of this sequence, the substituents present on the benzene ring are preferably the same substituents indicated above to be preferred. The product of this first reaction is a 5-amino-2,4,6-triiodo-N-(mono or poly)hydroxyalkyl-5'-(mono or poly)hydroxyalkyl-isophthalamide.

This first intermediate is then reacted with an acylating compound, preferably an acylhalide or acylanhydride, most preferably an acylhalide such as acetyl chloride, to give the 5-acylamino derivative. This derivative can also be prepared from an ionic iodinated compound (e.g., ioxithalamic acid), by protecting the hydroxyls by acetylation, by activating the carboxyl, especially with an acid halide, and by reacting with an appropriate hydroxyalkylamine, particularly 1-amino-2,3-propanediol. See Examples 3 and 25 for details of the appropriate reactions. This derivative is then reacted with an epihalohydrin as described previously. A preferred method is to dissolve the derivative in 1,2-propanediol containing sodium bicarbonate and epichlorohydrin. This reaction is typically completed in approximately 1 hr at 90° C.

A preferred starting material for use in this aspect of the invention is 5-amino-N-(2-hydroxyethyl)-N'-(2,3-dihydroxypropyl)isophthalamide, which is available commercially. Carrying out the reactions described above with KICl$_2$ acetylchloride, and epichlorohydrin gives 5-(2,3-dihydroxypropylacetamido)-2,4,6-triiodo-N-(2,3-dihydroxypropyl)-N'-(2hydroxyethyl)isophthalamide, compound VIII in the Experimental Section, which can also be prepared by the techniques previously described. However, this particular method produces the desired compound in only three steps from a commercially available source.

In preparing the subject compounds of the invention, an improved process for alkylating acylamidobenzene compounds has been discovered. The prior art has typically indicated that alkylation of such compounds with an alkylating agent, such as an alkylchloride or an epichlorohydrin, has required the presence of a weak organic base, such as triethylamine, or a strong organic base, such as sodium methoxide. It has been discovered that high yields of alkylated products can be achieved by carrying out the reaction in the presence of sodium bicarbonate. Typically, the acylamidobenzene compound is dissolved in an alcohol, typically an alcohol containing 2 to 4 carbon atoms and 1 to 3 oxy groups, such as 1,2-propanediol, and reacted with the alkylating agent, such as epichlorohydrin, in the presence of sodium bicarbonate. The reaction is particularly suited to converting acetamido compounds into the corresponding N-(2,3-dihydroxypropyl) acetamido compound.

The sodium bicarbonate is typically present in excess to ensure complete scavenging of any acid generated in the alkylation reaction. Example 37 of the following examples sets forth a complete example of this reaction, including times, temperatures, and molar ratios.

The subject compounds may be used as contrast media for angiography, urography and opacification of body cavities.

These novel compounds are suitable as opacifying compounds in all fields of application of water-soluble non-ionic X-ray contrast media, especially for intravasal, subarachnoid and various local applications for which presently available non-ionic contrast media are employed.

The subject compounds can be formulated in accordance with conventional techniques, using pharmaceutically acceptable organic or inorganic carrier substances suitable for parenteral or enteral application for administration to a patient. Conventional pharmaceutically acceptable carriers include but are not limited to water, saline solution, alcohols, vegetable oils, polyethylene glycols, gelatin, lactose, amylose, magnesium stearate, paraffin oils, fatty acid mono- and diglycerides, pentaerythritol fatty acid esters, hydroxymethylcellulose, polyvinyl pyrrolidone, talc, etc.

Other additives which are conventional in galenic pharmacy include stabilizers, such as sodium EDTAate, calcium disodium EDTAate, physiologically compatible buffers, sodium chloride, etc.

For parenteral application, useful solutions include oily or aqueous solutions, as well as suspensions or emulsions.

For intravenous administration, the subject compounds will normally be used in an aqueous medium, where the concentration will be about 15 to 80 vol. percent, the active agent per unit dosage being about 1 to 80 g, usually 20 to 70 g.

Preferred concentration in aqueous media will generally be from about 50–400 mg I/ml, preferably about 100–400 mg I/ml, with dosages running from about 5 to 500 ml.

The following examples are offered by way of illustration and not by way of limitation:

EXPERIMENTAL

Example 1. Alkylation of ioxithalamic acid

5-Acetamido-2,4,6-triiodo-N-(2-hydroxyethyl)isophthalamic acid (I) into:

5-(N-2,3-Dihydroxypropylacetamido)-2,4,6,-triiodo-N-(2-hydroxyethyl)-isophthalamic acid (II)

To ioxithalamic acid (161 g, 0.25 moles) was added 1N sodium hydroxide (250 ml) and the pH adjusted with 5N NaOH to 10.5–10.6 at 85°–90° C. 3-Chloro-1,2-propanediol (30.41 g, 0.275 moles) was added and the pH readjusted to 10.5–10.6 with 5N NaOH, followed by further additions at 1 hr (2.76, 0.025 moles) and at 2 hr (2.76 g, 0.025 moles). The reaction was complete at 2.5 hr by TLC.

Glacial acetic acid (5 ml) was added to pH 5, solvents were evaporated and the residue azeotroped with toluene (150 ml) to obtain 294 g of a mixture which was used without product isolation in the next step.

Example 2. Acetylation of N-alkylated ioxithalamic acid 5-(N-2,3-Dihydroxypropylacetamido)-2,4,6-triiodo-N-(2-hydroxyethyl)-isophthalamic acid (II) into:

5-(N-2,3-Diacetoxypropylacetamido)-2,4,6-triiodo-N-(2-acetoxyethyl)-isophthalamic acid (III)

The crude mixture (290 g) from step one, containing the title compound (250 mMoles), was suspended in acetic anhydride (500 ml) and pyridine (19.76 g, 250 mMoles) and mechanically stirred at 65° C. By TLC, the acetylation was complete after 3 hr.

The acetic anhydride and acetic acid were evaporated, and the residue azeotroped with toluene (100 ml $\times 2$). The residue was dissolved in saturated aqueous sodium bicarbonate (500 ml) and ethyl acetate (200 ml). The layers were separated, and the bicarbonate layer re-extracted with ethyl acetate (200 ml $\times 2$). The aqueous layer was acidified with concentrated hydrochloric acid to pH 0–1 to obtain a white precipitate which was extracted with ethyl acetate ($3 \times 200$ ml). The organic extracts were combined and washed with brine (100 ml), and dried over MgSO$_4$. Removal of the solvent gave 206 g of the product (III) as a white foam (97% yield).

Example 3. Acyl-chloride formation of N-alkylated, acetylated ioxithalamic acid 5-(N-2,3-Diacetoxypropylacetamido)-2,4,6-triiodo-N-(2-acetoxyethyl)-isophthalamic acid (III) into:
5-(N-2,3-Diacetoxypropylacetamido)-2,4,6-triiodo-N-(2-acetoxyethyl)-isophthalamic acid chloride (IV)

The title compound (III) (250 g, 243 mMoles) was dissolved in thionyl chloride (400 ml), and the reaction mixture heated at 60°–65° C. for 1 hr to completion (by TLC). The thionyl chloride was evaporated on a rotary evaporator, the residue azeotroped with ethyl acetate (250 ml ×2), the product dissolved in ethyl acetate (400 ml), extracted with aqueous saturated bicarbonate (150 ml ×2) and dried over MgSO4 to give 202 g of an off-white foam (96% yield).

Example 4. Amidation of alkylated, acetylated ioxithalamic acid chloride with trans-dioxepane (protected amino-threitol)

5-(N-2,3-Diacetoxypropylacetamido)-2,4,6-triiodo-N-(2-acetoxyethyl)-isophthalamic acid chloride (IV) into:
5-(N-2,3-Diacetoxypropylacetamido)-2,4,6-triiodo-N-2-acetoxyethyl)-N'-(trans-2,2-dimethyl-6-hydroxy-1,3,-dioxepan-5-yl)-isophthalamide (V)

The title compound (86.25 g, 100 mMoles) was dissolved in dimethylacetamide (200 ml) to which was added triethylamine (13.9 ml, 100 mMoles) and trans-5-amino-2,2-dimethyl-6-hydroxy-1,3-dioxepane (19.3 g, 120 mMoles). The reaction mixture was stirred at room temperature for 8 hr to completion (by TLC) The solvent was evaporated in vacuo and the residue dissolved in ethyl acetate (200 ml). The solution was washed with water (3x50 ml) and brine (2x50 ml). Drying (MgSO4) followed by solvent removal yielded the product (V) (96 g) as an off-white foam (97% yield).

Example 5. Deprotection of alkylated acetylated ioxithalamic acid amidated with trans-dioxepane to aminothreitol derivative 5-(N-2,3-Diacetoxypropylacetamido)-2,4,6-triiodo-N-(2-acetoxyethyl)-N'-(trans-2,2-dimethyl-6-hydroxy-1,3-dioxepan-5-yl)-isophthalamide (V) into:
5-(N-2,3-Dihydroxypropylacetamido)-2,4,6-triiodo-N-(2-hydroxyethyl)-N'-(1,3,4-trihydroxy-threo-but-2-yl)isophthalamide (VI)

The title compound (V) (4.94 g, 5 mMoles) was dissolved in methanol (20 ml), the pH was adjusted to 12-13 with 5N sodium hydroxide, and the mixture was agitated for 1 hr at 25° C. to achieve complete deacetylation (by TLC). Upon evaporation to dryness, 15 ml of 0.1N HCl was added (to pH 1-1.5), the solution stirred for 30 min at 25° C. to obtain the product (by HPLC) which, after evaporation of acid and redissolving in water, was desalted with AG-501 mixed bed ion exchange resin. The solution was decolorized with charcoal and the solvent removed in vacuo to obtain the product (VI) as a white powder (3.2 g) (78% yield).

Example 6. Amidation of alkylated, acetylated ioxithalamic acid with 3-amino-1,2-propanediol 5-(N-2,3-Diacetoxypropylacetamido)-2,4,6-triiodo-N-(2-acetoxyethyl)-isophthalamic acid chloride (IV) into:
5-(N-2,3-Diacetoxypropylacetamido)-2,4,6-triiodo-N-(2-acetoxyethyl)-N'-(2,3-dihydroxypropyl)-isophthalamide (VII)

The title compound (IV) (86.25 g, 100 mMoles) was dissolved in dimethylacetamide (200 ml) to which triethylamine (13.9 g, 100 mMoles) and 3-amino-1,2-propanediol (10.93 g, 120 mMoles) were added. The reaction was stirred at room temperature for 8 hr to completion by TLC. The solvent was evaporated in vacuo and the product dissolved in tetrahydrofuran (75 ml) and partitioned with water saturated with sodium chloride. The organic extract was washed with brine:1N hydrochloric acid (9:1, 50 ml ×2), followed by brine:water (1:1) (50 ml ×2) and finally brine (40 ml ×1). The organic layer was dried over MgSO4 and the solvent was removed to give 80.6 g of the product (VII) as an off-white foam (87.9% yield).

Example 7. Deprotection of alkylated, acetylated ioxithalamic acid amidated with 3-amino-1,2-propanediol 5-(N-2,3-Diacetoxypropylacetamido)-2,4,6-triiodo-N-(2-acetoxyethyl)-N'-(2,3-dihydroxypropyl)-isophthalamide (VII) into:
5-(N-2,3-Dihydroxypropylacetamido)-2,4,6-triiodo-N-(2,3-dihydroxypropyl)-N'-(2-hydroxyethyl)isophthalamide (VIII)

The title compound (VII) (9.17 g, 10 mMoles) was dissolved in methanol (20 ml), the pH adjusted to 13 with 5N sodium hydroxide and stirred at room temperature for 30min to achieve complete deacetylation (by TLC and HPLC). The solution was neutralized with Dowex 50 H+ resin, and evaporated to give 7.8 g of an off-white foam (99% yield). This product was dissolved in water and decolorized with charcoal. Removal of the solvent gave the product (VIII) as a white foam (6.3 g) (80% yield).

NMR: ($^1$H, 80 MHz, DMSO-d6): 8.6 (2 H, broadened multiplet, carbamoyl N-H): 4.9–4.0 (5 H, broad singlet, exchangeable, hydroxyl protons): 4.1–2.8 (14 H, multiplet,.protons on carbon bearing nitrogen and hydroxyl functions): 2.25 and 1.8 (3 H, pair of singlets, acetanilide methyl protons).

TLC: silica gel 70:30 CHCl3:MeOH: rf (acetylated compound VII) 0 84: rf (product compound VIII) 0.20.

HPLC: aminopropyl Alltech, 10μ, 31 ml/min of 87% acetonitrile/water.

rf: 6.1 and 7.5 for two isomers.

Elemental Analysis: Calculated for $C_{18}H_{24}I_3N_3O_8H_2O$: C26.71; H,3,26; I,47.05; N,5.19 %: Found: C,26.45, H,3.30: I,46.71: N,4.80%.

ALTERNATE SYNTHESIS OF COMPOUND (VIII)

Step 1. Alkylation of ioxithalamic acid

5-Acetamido-2,4,6-triiodo-N-(2-hydroxyethyl)isophthalamic acid (I) into:
5-(N-2,3-dihydroxypropylacetamido)-2,4,6-triiodo-N-(2-hydroxyethyl)-isophthalamic acid (II)

To the ioxithalamic acid (161 g, 0.25 moles) was added 1N sodium hydroxide (250 ml), followed by calcium hydroxide (13.4 g, 1.181 moles) and the suspension heated to 90° C. 1-Chloro-2,3-propanediol (37.3 g, 0.338 moles) was added over 2 hours. The reaction was complete at 2.5 hr by TLC.

Concentrated hydrochloric acid was added to 1 pH 5.0, solvents were evaporated and the residue azeotroped with acetic acid (200 ml) to obtain a mixture which was used without product isolation in the next step.

Step 2. Acetylation of N-alkylated ioxithalamic acid 5-(N-2,3-Dihydroxypropylacetamido)-2,4,6-triiodo-N-(2-hydroxyethyl)-isophthalamie acid (II) into:
5-(N-2,3-Diacetoxypropylacetamido)-2,4,6-triiodo-N-(2-acetoxyethyl)-isophthalamic acid (III)

The crude mixture from step one, containing the title compound (II) (185 g, 0.25 moles), was mixed with pyridine (19.76 g, 0.25 moles.), and acetic anhydride (240 ml, 2.54 moles) was added, maintaining the temperature at 70° C. By TLC, the acetylation was complete after 3 hr.

The acetic anhydride and acetic acid were largely evaporated, and the residue was dissolved in water (250 ml). The aqueous solution was washed with butyl acetate (50 ml×3) and then was acidified with concentrated hydrochloric acid to pH 0 to 1 to obtain a white precipitate which was extracted with dichloromethane (3×200 ml). The organic extracts were combined, the solvent removed and replaced with 1,2-dichloroethane (350 ml). Partial removal of the solvent gave a viscous solution that was dry enough for chlorination (containing the product in 93% yield).

Step 3. Acyl-Chloride formation of N-alkylated, acetylated ioxithalamic acid 5-(N-2,3-Diacetoxypropylacetamido)-2,4,6-triiodo-N-(2-acetoxyethyl)-isophthalamic acid (III) into:
5-(N-2,3-Diacetoxypropylacetamido)-2,4,6-triiodo-N-(2-aceteoxyethyl)-isophthalamic acid chloride (IV)

The title compound (III) (205 g, 0.243 moles) in 1,2-dichloroethane (total volume 250 ml) was mixed with thionyl chloride (53.2 ml, 0.79 moles) at 70° C., and the reaction mixture maintained at 70° C. for 2 hrs to completion (by TLC). The solvents were evaporated on a rotary evaporator, and the residue azeotroped with 1,2dichloroethane (100 ml ×2). The product was dissolved in 1,2-dichloroethane (200 ml), washed with aqueous saturated bicarbonate (150 ml ×1) and the solvent removed to give a viscous solution (containing the product IV in 96% yield).

Step 4. Amidation of 3-(N-2-acetoxyethyl)-carbamoyl-5-(N-2,3-diacetoxypropyl)-acetyl-amino-2,4,6triiodobenzoyl chloride (IV) with 3-aminopropane-1,2-diol into:

5-(N-2,3-Diacetoxypropylacetamido)-2,4,6-triiodo-N-(2-acetoxyethyl)-N'-(2,3-dihydroxypropyl)-isopthalamide (VII)

The title compound (IV) (240 g, 0.27 moles) in 1,2-dichloroethane (total volume 160 ml) was diluted with acetone (270 ml) and added to a mixture of 3-amino-1,2-propanediol (30.4 g, 0.334 moles), water (65 ml), and sodium bicarbonate (23.4 g, 0.278 moles). The mixture was heated at 55° C. for 8 hrs, when TLC indicated that the reaction had gone to completion. Water (500 ml) was added and the solution was extracted with 1,2-dichloroethane containing 15% by volume of acetone (2 × 40 ml). The aqueous layer was salted with sodium sulfate (140 g) and was extracted with a mixture of dichloromethane:n-propanol (9:1, 300 ml). The dichloromethane was removed at atmospheric pressure, n-propanol (300 ml) was added, and the solution was concentrated to a volume of 250 ml. This solution was treated with Dowex-50-H resin to remove the excess 3-amino-1,2-propanediol, and the solution was charcoaled overnight under reflux. The charcoal was removed and the filtrate was freed of the solvent to obtain an off-white foam (VII) (220 g).

TLC: (silica gel, 90% chloroform/10% methanol). RF (IV): 0 78 and 0.70. RF (V): 0.28.

Step 5. Deacetylation of 5-(N-2,3-diacetoxypropyl-acetamido)-2,4,6-triiodo-N-(2-acetoxyethyl)-N'-(2,3-dihydroxypropyl)-isophthalamide (VII) into:
5-(N-2,3-dihydroxypropylacetamido)-2,4,6-triiodo-N-(2-hydroxyethyl)-N'-(2,3-dihydroxypropyl)-isophthalamide (VIII)

The product from the previous amidation reaction (V) (220 g) was dissolved in methanol (450 ml) and 1M sodium methoxide in methanol (50 ml) was added. The solution was stirred for 30min, during which time methyl acetate was removed as an azeotrope with methanol. The final solution was neutralized to pH 7.0 by the addition of Dowex-50-H+. The solution was freed of solvent to obtain (VIII) as an off-white foam (184 g, 0.232 moles) (yield: 84% from the corresponding acid chloride). An aqueous solution of (VIII) (0.5 moles) was charcoaled (5% W/W) at 80° C. for 4 hrs, filtered, water removed, and the product recrystallized from 5% aqueous ethanol, to yield 87% of (VIII) 99.2% pure. (Analytical data: See Example 7).

Example 8. Amidation of alkylated, acetylated ioxithalamic acid chloride with diethanolamine 5-(N-2,3-Diacetoxypropylacetamido)-2,4,6-triiodo-N-(2-acetoxyethyl)-isophthalamic acid chloride (IV) into:
5-(N-2,3-Dihydroxypropylacetamido)-2,4,6-triiodo-N,N-bis-(2-hydroxyethyl)-N'-(2-hydroxyethyl)-isophthalamide (IX)

The title compound (IV) (4.31 g, 5 mMoles) was dissolved in dimethylacetamide (10 ml) and triethylamine (0.7 ml, 5 mMoles) and diethanolamine (0.79 g, 7.5 mMoles) were added. The reaction mixture was maintained at room temperature for 8 hr to completion by TLC. Following evaporation of the solvent in vacuo, residue was partitioned between tetrahydrofuran (50 ml) and brine (50 ml). The organic layer was washed with brine: conc. HCl (9:1, 15 ml × 1), followed by 75% saturated brine (20 ml ×3). The organic extracts were dried over MgSO$_4$ and the solvent removed to give 4.5 g of an off-white foam (94% yield). The material was deprotected as described in Example 7, and desalted on mixed bed resin (AG-501) to yield 4.2 g of final product (IX).

Example 9. Amidation of alkylated, acetylated ioxithalamic acid chloride with serinol 5-(N-2,3-Diacetoxypropylacetamido)-2,4,6-triiodo-N-(2-acetoxyethyl)-isophthalamic acid chloride (IV) into:
5-(N-2,3-Dihydroxypropylacetamido)-2,4,6-triiodo-N-(1,3-dihydroxyisopropyl)-N'-(2-hydroxyethyl)isophthalamide (X)

To the solution of the title compound (IV) (12.3 g, 14.3 mMoles) in dimethylacetamide (54 ml) was added triethylamine (2.0 ml: 14.3 mMoles) and serinol (1.56 g, 17.2 mMoles). The reaction mixture was stirred at room temperature for 8 hr to completion by TLC. The solvent was removed in vacuo and to the residue tetrahydrofuran (20 ml) and brine (20 ml) were added. The aqueous layer was extracted with tetrahydrofuran (2 × 10 ml). The organic layer was dried (MgSO$_4$) and the removal of the solvent gave an off-white solid (11.45 g), which was deacetylated as decribed in Example 38. Desalting of the crude product on Dowex mixed bed resin (AG-501), followed by decolorization with charcoal and evaporation, yielded the product (X) (10.1 g) (77% yield).

Example 10

5-Acetamido-2,4,6-triiodo-N-methylisophthalamic acid (XI) into:
5-(N-2,3-Dihydroxypropylacetamido)-2,4,6-triiodo-N-methylisophthalamic acid (XII)

Sodium iothalamate (XI) (146 g, 229.5 mMoles) was dissolved in 1N sodium hydroxide (380 ml), followed by addition (over 30min) of 3-chloro-1,2-propanediol (28.75 ml; 344 mMoles): pH was adjusted with 5N NaOH to 11.5-12.0. The mixture was brought to 85° C. and stirred for 2 hr to completion by TLC. The pH was adjusted to 6-7 with concentrated hydrochloric acid and the water removed on an evaporator The residue was azeotroped with toluene (100 ml × 1) to give 215 g (including inorganic salts) of an off-white product (XII) which without isolation was acetylated in the next reaction.

Example 11. Acetylation of the alkylated iothalamic acid 5-(N-2,3-Dihydroxypropylacetamido)-2,4,6-triiodo-N-methylisophthalamic acid chloride (XII) into:
5-(N-2,3-Diacetoxypropylacetamido)-2,4,6-triiodo-N-methylisophthalamic acid (XIII)

To the crude product (XII) (215 g) from Example 10 were added pyridine (25 ml) followed by acetic anhydride (400 ml) with the temperature maintained below 50° C. The mixture was heated at 50° C. for 1 hr and the solvents were removed in vacuo. The residue was coevaporated with toluene (2×100 ml) and dissolved in a mixture of ethyl acetate (300 ml) and aqueous sodium bicarbonate (750 ml). The aqueous layer was extracted with ethyl acetate (2×200 ml) and acidified with concentrated hydrochloric acid to pH 0.5. The mixture was extracted with ethyl acetate (3×300 ml) and the combined organic layers were washed with water (2×100 ml) and brine (2×50 ml) and dried (MgSO$_4$) Removal of the solvent gave the product (XIII), a light yellow foam (163 g) (92% yield from sodium iothalamate (XI)).

Example 12. Acylchlorination of the alkylated, acetylated iothalamic acid 5-(N-2,3-Diacetoxypropylacetamido)-2,4,6-triiodo-N-methylisophthalamic acid (XIII) into:
5-(N-2,3-Diacetoxypropylacetamido)-2,4,6-triiodo-N-methylisophthalamic acid chloride (XIV)

The product (XIII) of Example 11 (163 g. 0.21 mole) was dissolved in thionyl chloride (500 ml), stirred and refluxed for 1 hr, when TLC showed that the reaction was over. Thionyl chloride was distilled off at 50°-60° C. at 100 Torr and the residue dried by coevaporation with ethyl acetate (2×100 ml). The off-white foamy product was dissolved in ethyl acetate (700 ml), washed with saturated aqueous sodium bicarbonate (4×200 ml) and brine (2×250 ml). The organic layer was dried (MgSO$_4$) and the solvent removed to give the product (XIV) as an off-white foam (143.3 g) representing 79% yield as calculated from the iothalamic acid.

Example 13. Amidation of the chloride of the alkylated, acetylated iothalamic acid with cis-dioxepane 5-(N-2,3-Diacetoxypropylacetamido)-2,4,6-triiodo-N-methylisophthalamic acid chloride (XIV) into:
5-(N-2,3-Diacetoxypropylacetamido)-2,4,6-triiodo-N-(cis-2,2-dimethyl-6-hydroxy-1,3-dioxepan-5-yl)-N'-methylisophthalamide (XV)

The title compound (XIV) (10 g, 12.65 mMoles) was dissolved in dimethylacetamide (25 ml) to which triethylamine (1.8 ml, 12.65 mMoles) and cis-5-amino-2,2-dimethyl-6-hydroxy-1,3-dioxepane (2.44 g, 15.2 mMoles) were added. The solution was stirred at room temperature for 8 hr, when the reaction was complete. The solvent was removed in vacuo and the residue dissolved in ethyl acetate (50 ml). The solution was washed with water (3×25 ml) and brine (2×25 ml). Drying (MgSO$_4$), followed by solvent removal, gave the product (XV) as an off-white foam.

Example 14. Deprotection of alkylated, acetylated iothalamic acid amidated with cis-dioxepane to D,L-aminoerythritol derivative 5-(N-2,3-Diacetoxypropylacetamido)-2,4,6-triiodo-N-(cis-2,2-dimethyl-6-hydroxy-1,3-dioxepan-5-yl)-N'-methylisophthalamide (XV) into:
5-(N-2,3-Dihydroxypropylacetamido)-2,4,6-triiodo-N-methyl-N'-(1,3,4-trihydroxy-erythro-but-2-yl)-isophthalamide (XVI)

To a solution of the title compound (XV) (7.9 g, 8.63 mMoles) in methanol (30 ml) was added 5N NaOH to pH 13. By TLC, deacetylation was complete after 30 min at 24° C. The solution was treated with Dowex 50 H+ resin and the solvent was removed on a rotary evaporator to give 6.78 g foam (96% yield), which was dissolved in H$_2$O (30 ml). 1N HCl (3 ml) was added and the mixture stirred for 1 hr at 25° C. The solvents were removed on a rotary evaporator, and the residual acid removed with Dowex mixed-bed resin (AG-501). Charcoaling and evaporation gave 5.9 g of product (XVI) as a white foam (5.9 g) (86% yield).

Example 15. Amidation of alkylated, acetylated iothalamic acid chloride with protected D,L-aminothreitol 5-(N-2,3-Diacetoxypropylacetamido)-2,4,6-triiodo-N-methylisophthalamic acid chloride (XIV) into:
5-(N-2,3-Diacetoxypropylacetamido)-2,4,6-triiodo-N-(trans-2,2-dimethyl-6-hydroxy-1,3-dioxepan-5-yl)-N'-methylisophthalamide (XVII)

To the solution of the title compound (XIV) (11 g, 13.9 mMoles) in dimethylacetamide (25 ml) were added trimethylamine (1.9 ml: 13.9 mMoles) and trans-5-amino-2,2-dimethyl-6-hydroxy-1,3-dioxepane (2.69 g, 16.7 mMoles). The reaction mixture was stirred at room temperature for 8 hr to completion by TLC. The solvent was removed in vacuo and the residue dissolved in ethyl acetate (50 ml). The solution was washed with water (3 ×25 ml) and brine (2×25 ml). Drying (MgSO$_4$), followed by solvent removal, gave the product (XVII) as a pale yellow foam.

Example 16. Deprotection of alkylated, acetylated iothalamaic acid amidated with trans-dioxepane to D,L-aminothreitol derivative 5-(N-2,3-Diacetoxypropylacetamido)-2,4,6-triiodo-N-(trans-2,2-dimethyl-6-hydroxy-1,3-dioxepan-5-yl)-N'-methylisophthalamide (XVII) into:
5-(N-2,3-Dihydroxypropylacetamido)-2,4,6-triiodo-N-methyl-N'-(1,3,4-trihydroxy-threo-but-2-yl)isophthalamide (XVIII)

To a solution of the title compound (XVII) (4.5 g, 4.92 mMoles) in methanol (15 ml) was added 5N NaOH to pH 13. By TLC, deacetylation was complete after 30 min at 24° C. The solution was treated with Dowex 50-H+ resin and the solvent removed on a rotary evaporator to give 4.30 g foam, which was dissolved in H$_2$O (30 ml). 1N HCl (30 ml) was added and the solution stirred for 1 hr at 25° C. The solvents were removed on a rotary evaporator, and the residual acid removed with Dowex mixed-bed resin (AG-501). Charcoaling and evaporation gave the product (XVIII) as a white foam (3.6 g) (93% yield).

Example 17. Alkylation of metrizoic acid with chloropropanediol

3Acetamido-5-(N-methylacetamido)-2,4,6-triiodobenzoic acid (XIX) into:
3-(N-2,3-Dihydroxypropylacetamido)-5-(N-methylacetamido)-2,4,6-triiodobenzoic acid (XX)

The title compound (XIX) as the sodium salt (15 g, 23.1 mMoles) was dissolved in 100 ml water to which 5N sodium hydroxide was added to pH 12-13. 3-Chloro-1,2-propanediol (2.81 g, 25.4 mMoles) was added dropwise over 15 min, and the pH adjusted to 12-13 with additional 5N sodium hydroxide. After 1.5 hr at 50-60° C., the reaction was indicated as completed by TLC: 2N HCl was added to pH 7 and the solvents removed in vacuo. The residue was dried by coevaporation with pyridine. The resulting foamy product (XX), weighing 26.1 g and containing inorganic salt, was used directly in Example 18.

Example 18: Acetylation of N-alkylated metrizoic acid 3-(N-2,3-Dihydroxypropylacetamido)-5-(N-methylacetamido)-2,4,6-triiodobenzoic acid (XX) into:
3-(N-2,3-Diacetoxypropylacetamido)-5-(N-methylacetamido)-2,4,6-triiodobenzoic acid (XXI)

The crude product (26.1 g) produced in Example 17 was suspended in acetic anhydride (26.2 ml 77 mMoles) to which pyridine (25 ml) was also added. Upon stirring, at 50° C., for 1 hr, the reaction was complete by TLC. The solvents were removed in vacuo and the residue was co-evaporated with toluene (2×20 ml) and dissolved in a mixture of ethyl acetate (100 ml) and aqueous sodium bicarbonate (100 ml). The aqueous layer was extracted with ethyl acetate (2×5 ml) and acidified with concentrated hydrochloric acid to pH 0.5. The mixture was extracted with ethyl acetate containing 10% of tetrahydrofuran (3×50 ml) and the combined organic layers were washed with water (2×25 ml) and brine (2×25 ml) and dried (MgSO$_4$). Removal of the solvent gave the product (XXI) as an off-white solid (17.5 g) (96% yield based on metrizoic acid).

Example 19. Acylchlorination of acetylated, alkylated metrizoic acid 3-(N-2,3-Diacetoxypropylacetamido)-5-(N-methylacetamido)-2,4,6-triiodobenzoic acid (XXI) into
3-(N-2,3-Diacetoxypropylacetamido)-5-(N-methylacetamido)-2,4,6-triiodobenzoyl chloride (XXII)

The title compound (XXI) (15 g, 19.1 mMoles) was suspended in thionyl chloride (40 ml) and heated to reflux with stirring. At 1 hr, TLC indicated completion of the reaction. Thionyl chloride was distilled off in vacuo. Following dissolution in 40 ml chloroform and extraction with 40 ml saturated bicarbonate, washing with water and brine, the organic layer was dried over MgSO$_4$, filtered and solvents evaporated on a Rotovap to yield the product (XXII) (14.6 g) (95% yield) as a yellow solid. MP 145°-150° C. (dec).

Example 20. Amidation of metrizoic acid chloride (previously acetylated and alkylated) with trans-dioxepane 3-N-2,3-Diacetoxypropylacetamido)-5-(N-methyl-acetamido)-2,4,6-triiodobenzoyl chloride (XXII) into:
3-(N-2,3-Diacetoxypropylacetamido)-5-(N-methylacetamido)-2,4,6-triiodo-N-(trans-2,2-dimethyl-6-hydroxy-1,3-dioxepan-5-yl)-benzamide (XXIII)

The title compound (XXII) (8 g; 9.94 mMoles) was dissolved in dimethylacetamide (20 ml) and to this solution were added triethylamine (1.4 ml: 9.96 mMoles) and trans-5-amino-2,2-dimethyl-6-hydroxy-1,3-dioxepane (1.9 g; 11.9 mMoles). The reaction mixture was stirred at room temperature for 8 hr, when the reaction was complete by TLC. The solvent was removed in vacuo and the residue dissolved in dichloromethane (40 ml). The solution was washed with water (3×25 ml) and brine (2 ×25 ml). Drying (MgSO$_4$), followed by solvent removal, gave the product (XXIII) as a yellow foam (9.29 g) (99% yield).

Example 21. Deprotection of alkylated metrizoic acid with trans-dioxepane to D,L-aminothreitol derivative 3-(N-2,3-Diacetoxypropylacetamido)-5-(N-methyl-acetamido)-2,4,6-triiodo-N-(trans-2,2-dimethyl-6-hydroxy-1,3-dioxepan-5-yl)-benzamide (XXIII) into:
3-(N-2,3-Dihydroxypropylacetamido)-5-(N-methylacetamido)-2,4,6-triiodo-N-(1,3,4-trihydroxy-threo-but-2-yl)-benzamide (XXIV)

The title compound (XXIII) (5 g, 5.38 mMoles) was dissolved in 23 ml methanol and 2.7 ml of 0.2M sodium hydroxide in methanol was added. After 1.5 hr the solution was evaporated to dryness (4.3 g, 94% yield), to which 13 ml water and 0.025 ml of concentrated HCl (0.3 mMoles) was added. After 2 hr of stirring the solution was neutralized with 1.26 ml 1N sodium hydroxide and desalted on a mixed bed AG-501 ionic exchange resin to obtain the product (XXIV) as an off-white solid (3.27 g) (75% yield).

Example 22. Alkylation and subsequent acetylation of diatrizoic acid 3,5-Diacetamido-2,4,6-triiodobenzoic acid (diatrizoic acid) (XXV) into:
3,5-bis-(N-2,3,-Diacetoxypropylacetamido)-2,4,6triiodobenzoic acid (XXVI)

Diatrizoic acid (XXV) (205.6 g, 0.33 mole) was dissolved in 6.45N aqueous sodium hydroxide (160 ml). The solution was heated to 45° C. and with mechanical stirring 3-chloro-1,2-propanediol (77.9 g, 0.7mole) was added dropwise during 15min. The reaction mixture was heated at 45° C. for 5 hr and then neutralized to pH 7.0 by the addition of concentrated hydrochloric acid (2.4 ml) The solvent was removed in vacuo at 50° C. and the residue was dried by azeotropic distillation with pyridine (3×150 ml). To the resulting white foam (345 g) were added pyridine (100 ml: 1.27 moles) and acetic anhydride (260 ml: 2.76 moles) with cooling to maintain the temperature at 40° C. The mixture was heated at 40° C. for 1 hr, and then treated with water (100 ml), with ice-cooling, for 30min. The solution was diluted with water (500 ml) and extracted with a mixture of ethyl acetate/toluene (1:3) (4×200 ml). The aqueous layer was acidified to pH 0-1 with concentrated hydrochloric acid, the product was taken up in ethyl acetate (500 ml) and the organic solution was washed with 10% sodium chloride (5×300 ml), followed by brine (2×100 ml Drying (MgSO$_4$) followed by solvent removal yielded the product (XXVI) as a white foam (260 g) (85% yield from diatrizoic acid) (XXV).

Example 23: Amidation of alkylated, acetylated ioxithalamic acid chloride with diethanolamine 5-(D-2,3-Diacetoxypropylacetamido)-2,4,6-triiodo-N-(2-acetoxyethyl)-isophthalamic acid chloride (IV) into:
5-(N-2,3-Diacetoxypropylacetamido)-2,4,6-triiodo-N-N-bis-(2-hydroxyethyl)-N'-(2-acetoxyethyl)-isophthalamide (XXVII) (Refer also to Example 8)

To a solution of (IV) (4.31 g, 5 mMoles) in dioxane (10 ml) and water (2 ml) was added solid potassium carbonate (0 691 g, 5 mMoles), diethanolamine (0.790 g, 7.5 mMoles) and the mixture heated to 50°-55° C. for 2-3 hrs when the reaction was complete by TLC.

The reaction mixture was partitioned between tetrahydrofuran (50 ml) and brine (50 ml), and the layers separated. The organic layer was washed with brine:-conc. HCl (9:1, 15 ml ×1), followed by 75% saturated brine (20 ml ×3). The THF extracts were dried over MgSO$_4$ and the solvent removed to give 4.2 g (XXVII) (90% yield).

Example 24: Deprotection of alkylated, acetylated ioxithalamic acid amidated with diethanolamine 5-(N-2,3-Diacetoxypropylacetamido)-2,4,6-triiodo-N,N-bis-(2-hydroxyethyl)-N'-(2-acetoxyethyl)-isophthalamide (XXVII) into:
5-(N-2,3-Dihydroxypropylacetamido)-2,4,6-triiodo-N,N-bis-(2-hydroxyethyl)-N'-(2-hydroxyethyl)-isophthalamide (IX)

A solution of (XXVII) (3.8 g, 4.1 mMoles) in methanol (20 ml) was treated with sodium methoxide (1M in methanol, 2 ml) at 25° C. The methyl acetate formed was continuously distilled off in vacuo. After 30 min, the solution was neutralized with Dowex 50H resin and the solvent removed to give (IX) (2.85 g, 87% yield).

Example 25: Amidation of alkylated acetylated ioxithalamic acid chloride with 3-N-methylamino-1,2-propanediol 5-(N-2,3-diacetoxypropylacetamido)-2,4,6-triiodo-N-(2-acetoxyethyl)-isophthalamic acid chloride (IV) into:
5-(N-2,3-diacetoxypropylacetamido)-2,4,6-triiodo-N-methyl-N-(2,3-dihydroxypropyl)-N'-(2-acetoxyethyl)isophthalamide (XXVIII)

The chloride (IV) (43.13 g, 50 mMoles) was dissolved in a mixture of acetone (70 ml) and water (20 ml), sodium bicarbonate (4.20 g, 50 mMoles), and 3-(N-methyl)-amino-1,2-propanediol (5.78 g, 55 mMoles).

The reaction mixture was heated at 50° C. for 4 hrs, then poured into water (400 ml) and 1,2-dichloroethane (50 ml) which gave two layers. The 1,2-dichloroethane layer was back-extracted with water (50 ml ×1). Anhydrous sodium sulfate (200 g) was added to the combined aqueous extracts, which were extracted with dichloromethane (250 ml ×1). Evaporation of the solvent gave 35.5 g of a white solid (XXVIII) (77% yield).

Example 26 Deprotection of alkylated, acetylated ioxithalamic acid amidated with 3-N-methyl-1,2-propanediol 5-(N-2,3-Diacetoxypropylacetamido)-2,4,6-triiodo-N,N-(methyl-2,3-dihydroxypropyl)-N'-(2-acetoxyethyl)isophthalamide (XXVIII) into:
5-(N-2,3-Dihydroxypropylacetamido)-2,4,6-triiodo-N-methyl-N-(2,3-dihydroxypropyl)-N'-(2-hydroxyethyl)isopthalamide (XXIX)

The title compound (XXVIII) (0.8 g, mMoles) was dissolved in methanol (1 ml) to which 0.5 ml of 1M sodium methoxide solution was added at 25° C., under stirring. The methyl acetate generated was continuously distilled off. After 30 min, the mixture was neutralized with Dowex 50 H resin and evaporated to give 0.677 g of a solid (XXIX) (98% yield).

Example 27. Amidation of alkylated, acetylated ioxithalamic acid chloride with 3-amino-1,2-propanediol 5-(N-2,3-Diacetoxypropylacetamido)-2,4,6-triiodo-N-(2-acetoxyethyl)-isophthalamic acid chloride (IV) into:
5-(N-2,3-Diacetoxypropylacetamido)-2,4,6-triiodo-N-(2,3-dihydroxypropyl)-N'-(2-acetoxyethyl)-isophthalamide (VII) (Refer also to Example 7, Alternate Synthesis)

The title compound (IV) (240 g, 0.27 mMoles) in 1,2-dichloroethane (total volume 160 ml) was diluted with acetone (270 ml) and added to a mixture of 3-amino-1,2-propanediol (30.4 g, 0.334 mMoles), water (65 ml), and sodium bicarbonate (23.4 g, 0 278 mMoles). The mixture was heated at 55° C. for 8 hrs, when TLC indicated the reaction was complete. Water (500 ml) was added and the solution was extracted with 1,2-dichloroethane (2×40 ml) containing 15% (by volume) of acetone. The aqueous layer was salted with sodium sulfate (140 g) and extracted with a mixture of dichloromethane: n-propanol (9:1, 300 ml). The dichloromethane was distilled off, n-propanol (300 ml) was added, the solution concentrated to 250 ml, and treated with Dowex-50-H+ resin, and charcoaled for 6 hrs under reflux. Filtration and solvent removal gave (VII) (220 g, 86% yield).

Example 28. Deprotection of alkylated, acetylated ioxithalamic acid amidated with 3-amino-1,2-propanediol 5-(N-2,3-Diacetoxypropylacetamido)-2,4,6-triiodo-N-(2,3-dihydroxypropyl)-N'-(2-acetoxyethyl)isophthalamide (VII) into:
5-(N-2,3-Dihydroxypropylacetamido)-2,4,6-triiodo-N-(2,3-dihydroxypropyl)-N'-(2-hydroxyethyl)isophthalamide (VIII) (Refer also to Example 7, Alternate Synthesis)

The product of the previous amidation reaction (VII) (220 g) was dissolved in methanol (450 ml) and 1M sodium methoxide in methanol (50 ml) was added. The solution was stirred for 30min, while methyl acetate was continuously removed in vacuo, then neutralized to pH 7.0 by Dowex-50-H+. Solvent removal gave a solid (VIII) (184 g, 0.232 moles) (yield: 84% from (IV) acid chloride).

Example 29. Acetylation of 5-amino-2,4,6-triiodo-N-(2,3-dihydroxypropyl)-isophthalamic acid 5-amino-2,4,6-triiodo-N-(2,3-dihydroxypropyl)isophthalamic acid (XXX) into:
5-acetamido-2,4,6-triiodo-N-(2,3-diacetoxypropyl)isophthalamic acid (XXXI)

The title compound (XXX) (252.8 g, 0.4 moles) was mixed with glacial acetic acid (150 ml) and acetic anhydride (350 ml, 3.7 moles). Concentrated sulfuric acid was added (10 ml) and the solution was heated for 6 hr at 40° C. The suspension was poured into a mixture of ice and brine (2:1, 1.5L) stirred for 30min and filtered off. The solid was washed with cold water (200 ml ×1) and dried to give 274 g (90% yield of (XXXI).

Example 30. Alkylation, followed by acetylation of 5-acetamido-2,4,6-triiodo-N-(2,3-dihydroxypropyl)-isopthalamic acid 5-acetamido-2,4,6-triiodo-N-(2,3-diacetoxypropyl)isophthalamio acid (XXXI) into:
5-(N-2,3-diacetoxypropylacetamido)-2,4,6-triiodo-N-(2,3-diacetoxypropyl)-isophthalamic acid (XXXII)

The title compound (XXXI) (227.4 g, 0.3 moles) was dissolved in 1N sodium hydroxide (300 ml) and pH adjusted to 12.0 by addition of 5N sodium hydroxide.

Calcium hydroxide (97%, 17 g, 0.223 moles) and 3-chloro-1,2-propanediol (44.76 g, 0.405 moles) were added at 85°–90° C. over two hours. After 2.5 hrs the reaction was complete by TLC.

The pH was brought to 6.0 by concentrated hydrochloric acid (4 ml), and water removed to give an oil which was dissolved in glacial acetic acid (500 ml). The solution was concentrated by 50% and pyridine (24.2 ml, 0.3 moles) and acetic anhydride (311 ml, 3.3 moles) were added over 45min. After 6 hr at 70° C., TLC indicated the reaction was complete.

Upon volume reduction to 50%, ice-cold water (500 ml) and ethyl acetate (250 ml) were added, the layers separated and the aqueous layer acidified to pH 1.0 with concentrated hydrochloric acid (60 ml). The product was extracted into dichloromethane (500 ml), which was then replaced with 1,2-dichloroethane (400 ml) to give 211.6 g, 0.231 moles of (XXXII) (77% yield).

Example 31. Chlorination of alkylated, acetylated 5-acetamido-2,4,6-triiodo-N-(2,3-dihydroxypropyl)-isophthalamide 5-N-(2,3-diacetoxypropylacetamido)-2,4,6-triiodo-N-(2,3-diacetoxypropyl)-isophthalamic acid (XXXII) into:
5-N-(2,3-diacetoxypropylacetamido)-2,4,6-triiodo-N-(2,3-diacetoxypropyl)-isophthalamic acid chloride (XXXIII)

To a solution of the title compound (XXXII) (169.5 g, 0.185 moles) in 1,2-dichloroethane (total volume 450 ml) at 55° C. was added thionyl chloride (51.25 ml, 0.702 moles). The solution was heated at 70° C. for 3 hr, when TLC showed the reaction was complete.

The solution was concentrated to 250 ml and the residue azeotroped with 1,2-dichloroethane (200 ml ×2). 700 ml of 1,2-dichloroethane was added and the mixture washed with saturated sodium bicarbonate (500 ml ×1) to give (XXXIII) (165.25 g, 96% yield).

Example 32. Amidation of alkylated, acetylated 5-acetamido-2,4,6-triiodo-N-(2,3-dihydroxypropyl)-isophthalamic acid chloride with 2-aminoethanol 5-(N-2,3-diacetoxypropylacetamido)-2,4,5-triiodo-N-2,3-diacetoxypropyl)-isophthalamic acid chloride (XXXIII) into:
5-(N-2,3-diacetoxypropylacetamido)-2,4,6-triiodo-N-(2-hydroxyethyl)-N'-(2,3-diacetoxypropyl)-isophthalamide (XXXIV)

The title compound (XXXIII), (132 g, 0.141Moles) was dissolved in acetone (300 ml) and water (75 ml), and to this was added sodium bicarbonate (11.85 g, 0.141Moles) and 2-aminoethanol (10.35 g, 0.170Moles). The reaction mixture was heated at 50° C. for 6 hr, when TLC showed that the reaction was complete.

The reaction mixture was diluted with water (500 ml) and toluene (200 ml), and the layers were separated.

The organic layer was back-extracted with water (100 ml×1), the aqueous extracts combined and saturated with sodium chloride, and the product was extracted with dichloromethane (400 ml). The dichloromethane layer was washed with 50% brine solution (50 ml×1), the layers separated and the dichloromethane removed to give XXXIV (120.6 g, 89% yield).

Example 33. Deprotection of alkylated, acetylated 5-(N-2,3-dihydroxypropylacetamido)-2,4,b-triiodo-isopthalamic acid amidated with 2-amino ethanol 5-(N-2,3-diacetoxypropylacetamido)-2,4,6-triiodo-N-(2-hydroxyethyl)-N'-(2,3-diacetoxypropyl)-isophthalamide (XXXIV) into:
5-(N-2,3-dihydroxypropylacetamido)-2,4,6-triiodo-N-(2-hydroxyethyl)-N'-(2,3-dihydroxypropyl)-isophthalamide (VIII)

The title compound (XXXIV) (60.3 g, 0.063 moles) was dissolved in methanol (total volume 50 ml). 15 ml of a 1M solution of sodium methoxide were added and the solution stirred for 30min at 25° C. while the methyl acetate generated was continuously distilled off in vacuo. The solution was then neutralized with Dowex 50-H+ and the solvent removed to give VIII (49.1 g, 99% yield).

Example 34. Alkylation of acetylated ioxithalamic acid 5-acetamido-2,4,6-triiodo-N-(2-acetoxyethyl)isophthalamic acid (XXXV) into:
5-(N-2,3-dihydroxypropylacetamido)-2,4,6-triiodo-N-(2- hydroxyethyl)-isophthalamic acid (II)

The title compound (XXXV) (6.86 g, 0.01 moles) was dissolved in 1N sodium hydroxide (10 ml) and 10N sodium hydroxide (1 ml) was added to saponify the ester.

The solution was heated to 90° C. and calcium hydroxide (97%, 0.556 g, 0.0075 moles) was added followed by 3-chloro-1,2-propanediol (1.5 g, 0.0135 moles) over 1 hour. The reaction was heated for an additional 30 minutes to completion by TLC.

Glacial acetic acid was added to pH 5.0, solvents were evaporated and the residue azeotroped with toluene (20 ml) to obtain 11.7 g of a mixture amenable to acetylation as shown in Example 2.

ALTERNATIVE SYNTHESIS OF COMPOUND VIII: EXAMPLES 35-37

Example 35. Iodination of 5-amino-N-(2-hydroxyethyl)-N'-(2,3-dihydroxypropyl)isophthalamide (hydrochloride)

5-amino-N-(2-hydroxyethyl)-N'-(2,3-dihydroxypropyl)isophthalamide (hydrochloride) (XXXVI) into:
5-amino-2,4,6-triiodo-N-(2-hydroxyethyl)-N'-(2,3-dihydroxypropyl)-isophthalamide (XXXVII):

The title compound (XXXVI, 600 mg, 1 80 mMoles was dissolved in water (8.9 ml) and conc. hydrochloric acid (0.15 ml). 1.84M KICl$_2$ (3.3 ml) was added and the reaction was heated at 80° C. for 3 hours. Reaction pH was adjusted with sodium bicarbonate, rotovaped to dryness, and dissolved in 8 ml ethanol. Inorganic salts were filtered off, the filtrate acidified with conc. HCl, and evaporated to give 918 mg of an orange solid (79% yield).

Example 36: Acetylation of 5-amino-2,4,6-triiodo-N-(2-hydroxyethyl)-N'-(2,3-dihydroxypropyl)-isophthalamide 5-amino-2,4,6-triiodo-N-(2-hydroxyethyl)-N'-(2,3-dihydroxypropyl)-isophthalamide (XXXVII) into:
5-acetamido-2,4,6-triiodo-N-(2-acetoxyethyl)-N'-(2,3-diacetoxypropyl)-isophthalamide (XXXVIII):

The title compound (600mg, 0.89 mMoles) was dissolved into glacial acetic acid (1 ml): pyridine (72μL, 0.89 mMoles) and acetyl chloride (620μL, 8.9 mMoles) were added and the reaction was heated at 50° C. for 2 hours to completion by TLC.

The excess acetyl chloride was removed by distillation, the product dissolved in tetrahydrofuran (10 ml) and the solution was washed with a brine-0.1 N HCl mixture (5 ml×1). The THF was removed to give 650 mg of the product (XXXVIII) (87% yield).

Example 37: Alkylation of 5-acetamido-2,4,6-triiodo-N-(2-acetoxyethyl)-N'-(2,3-diacetoxypropyl)isophthalamide with epichlorohydrin 5-acetamido-2,4,6-triiodo-N-(2-acetoxyethyl)-N'-(2,3-diacetoxypropyl)-isophthalamide (XXXVIII) into:
5-N-(2,3-dihydroxypropyl)-acetamido-2,4,6-triiodo-N-(2-hydroxyethyl)-N'-(2,3-dihydroxypropyl)-isophthalamide (VIII)

The title compound (XXXVIII, 650 mg, 0.77 mMoles) was dissolved in 1,2-propanediol (3 ml), sodium bicarbonate (1.29 mg, 1.54 mMoles) and epichlorohydrin (1.2 ml, 15.4 mMoles) were added and the reaction was heated at 90° C. TLC and HPLC showed that the reaction was complete at 1 hour to yield compound VIII, in 73% yield.

Example 38: Deacetylation of alkylated, acetylated ioxithalamic acid chloride (IV) amidated with serinol 5-(N-2,3-diacetoxypropylacetamido)-2,4,6-triiodo-N-(2-acetoxyethyl)-N-(1,3-dihydroxyisopropyl)isophthalamide (XXXIX) into:
5-(N-2,3-dihydroxypropylacetamido)-2,4,6-triiodo-N-(1,3-dihydroxyisopropyl-N'-(2-hydroxyethyl)isophthalamide (X)

The title compound (XXXIX, 11.45 g, 0.0125moles) was dissolved in methanol (25 ml), the pH adjusted to 13 using 5N sodium hydroxide, and the solution was stirred at room temperature for 30 minutes to achieve complete deacetylation, as determined by HPLC and TLC. The solution was neutralized with Dowex 50 H+ resin, and the solvent was removed to give an off-white foam. Desalting of the crude product on Dowex mixed-bed resin (AG-501), followed by decolorization with charcoal and evaporation, yielded the product (X, 8.7 g, 77% yield).

The above procedures demonstrated the simple, rapid and efficient synthesis strategy of the subject invention. The economics of the method are evidenced by high yields and use of intermediates without further purification. In addition, only simple inexpensive and readily removable reagents are employed and the resulting product is substantially free of impurities. The number of steps from the starting material is minimal to further minimize separations and purifications.

All compounds were tested for stability, solubility, osmolality, viscosity and systemic toxicity, using conventional tests. Compounds VIII and XVI were tested with existing compounds serving as control and shown to have substantially reduced osmolality while having comparable or superior properties in the other categories.

TABLE

Properties of Preferred Novel Compounds and of the Prior Art Non-Ionic CM*

|  | Compound VIII | Compound XVI | Iopromide | Iohexol | Iopamidol |
|---|---|---|---|---|---|
| Osmolality (mOsm/kg) | 524 | 513 | 607+ | 690+ | 619+ |
| Viscosity (cps) | 4.9 | 5.2 | 4.8+ | 6.1+ | 4.5+ |
| i.v. LD50 (gI/kg)* |  |  |  |  |  |
| Mice (female CD-1) | 18.8 (18–19.5)++ | 12–13 | 11.5–13.0 | 17.9 (17.2–18.6)++ | 17–18.5 |
| Rats (female Lewis) | 14–16.5 | 13.5–14 | 10–11.5 | 13.5–15 | 12.2–13 |

*All at 300 mg I/ml concentration and 37° C. Injection rates 1 ml/min in mice and 5 ml/min in rats.
+Ref. Handbook of Experimental Pharmacology, Vol. 73, M. Sovak, ed., Springer-Verlag 1984, Table 1, p. 9.
'Ref. Salvesen, S. in Acta Radiol. Suppl. 362, p. 73, 1980.
++Confidence limit, indicating no statistically significant difference.

It is evident from the above results that the subject compounds provide improvement in contrast media since, in angiography, hyperosmolality causes vascular pain and contrast media solutions of less than 600 mOsm are known to be painless. The combination of low viscosity with low osmolality has never previously been obtained in a clinically useful contrast medium.

All publications cited in this specification are indicative of the level of skill of those skilled in the art to which this invention pertains and are individually incorporated herein by reference to the same extent as if each individual publication had been individually incorporated by reference.

Although the foregoing invention has been described in some detail by way of illustration and example for purposes of clarity and understanding, it will be obvious that certain changes and modifications may be practiced within the scope of the appended claims.

What is claimed is:

1. A contrast medium formulation comprising 5-(N-2,3-dihydroxypropylacetamido)-2,4,6-triiodo-N-(23,-dihydroxypropyl)-N'-(2-hydroxyethyl)-isophthalamide in a physiologically acceptable medium at a concentration in the range of about 50 to 400 mg I/ml.

2. 5-(N-b 2,3-dihydroxypropylacetamido)-2,4,6-triiodo-N-(2-3,-dihydroxypropyl)-N'-( 2-hydroxyethyl)-isophthalamide.

* * * * *

UNITED STATES PATENT AND TRADEMARK OFFICE

CERTIFICATE EXTENDING PATENT TERM
UNDER 35 U.S.C. § 156

PATENT NO.      :   4,954,348

ISSUED          :   September 4, 1990

INVENTOR(S)     :   Milos Sovak et al.

PATENT OWNER    :   Cook Imaging Corporation

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of

839 days from September 4, 2007, the original expiration date of the patent, subject to the payment of maintenance fees as provided by law, with all rights pertaining thereto as provided by 35 U.S.C. § 156(b).

I have caused the seal of the Patent and Trademark Office to be affixed this 27th day of February 1998.

Bruce A. Lehman
Assistant Secretary of Commerce and
Commissioner of Patents and Trademarks